United States Patent [19]

Reiber

[11] Patent Number: 4,821,432
[45] Date of Patent: Apr. 18, 1989

[54] WALKING ADAPTER FOR POSTSURGICAL SHOES

[76] Inventor: M. Andrew Reiber, 16050 Bay Point Boulevard, N.E. 301, N., Ft. Myers, Fla. 33917

[21] Appl. No.: 173,570

[22] Filed: Mar. 25, 1988

[51] Int. Cl.$^4$ .................... A43B 13/00; A61F 05/04
[52] U.S. Cl. ........................ 36/110; 36/132; 128/835
[58] Field of Search ............ 36/73, 71.5, 110, 7.7, 36/7.6, 11.5, 108, 132, 136; 128/83, 83.5, 589, 623

[56] References Cited

U.S. PATENT DOCUMENTS

| | | | |
|---|---|---|---|
| 2,634,723 | 4/1953 | Wright | 128/83.5 |
| 2,884,717 | 5/1959 | Goldberg | 128/589 |
| 3,198,192 | 8/1965 | O'Brien | 128/83.5 |
| 3,661,151 | 5/1972 | Schoenbrun et al. | 128/83.5 |
| 3,680,550 | 8/1972 | Tunstall | 128/83.5 |
| 3,916,538 | 11/1975 | Loseff | 128/83.5 |
| 4,081,918 | 4/1978 | O'Brien | 36/132 |
| 4,206,558 | 6/1980 | Bivona | 36/7.5 |
| 4,246,706 | 1/1981 | Persons, Jr. | 36/73 |
| 4,360,011 | 11/1982 | Lems, Jr. | 128/83.5 |
| 4,461,289 | 7/1984 | Didier et al. | 128/83.5 |

FOREIGN PATENT DOCUMENTS

| | | | |
|---|---|---|---|
| 2032540 | 1/1972 | Fed. Rep. of Germany | 128/83.5 |
| 1533522 | 7/1968 | France | 36/110 |
| 840541 | 7/1960 | United Kingdom | 36/71.5 |

OTHER PUBLICATIONS

Journal of the A.M.A., "Self Adhering Nylon Tapes" vol. 168, No. 7 10/1958, Gershman M.D.

Primary Examiner—Steven N. Meyers
Attorney, Agent, or Firm—Charles J. Prescott

[57] ABSTRACT

A walking adapter connectable onto the ground-engaging surface or sole of a surgical sandal. The adapter comprises a rigid, configured support having a generally flat upper surface with adhesive means thereon for attachment transversely onto to the central portion of the sandal sole and a contoured lower surface which downwardly extends to its mid-portion. The mid-portion, relatively narrow and extending along the length of the adapter, is generally parallel to and spaced furthest from the upper surface and having ground-engaging surface texture. Various cross-section configurations and rib patterns are provided and the invention may also be releasably attachable for proper fore and aft adjustment and made lockably rotatable to modify the pivotal axis of the sandal during walking.

14 Claims, 1 Drawing Sheet

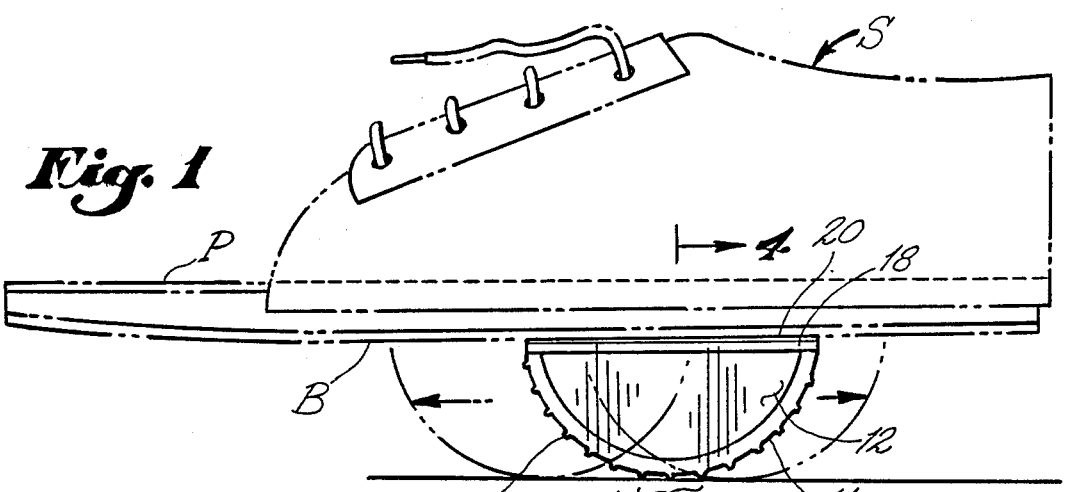

WALKING ADAPTER FOR POSTSURGICAL SHOES

BACKGROUND OF THE INVENTION

This invention relates generally to shoes in the field of healthcare, and more particularly to a walking adapter for use in conjunction with postsurgical sandals.

After foot surgery, the patient's foot is generally required to be maintained in an unflexed and unflexing state while recovering. This is required to allow wounds and stitching from surgery to remain stable to more quickly heal. In other situations relating to foot maladies, the medical practitioner there also may require that the entire foot be stablized and held in a flat unflexing position during the recovery period. However, in the majority of the above-referenced medical recouperative situations, the patient is otherwise able to ambulate.

Many inventions and devices are presently available to accomplish the task of maintaining the patient's foot in this unflexed and unflexing condition. A common well-known device is in the form of a postsurgical sandal comprising a rigid planer platform generally having parallel surfaces both top and bottom, the top surface may be padded slightly to eliminate bone pressure against the otherwise rigid platform, while the bottom surface may include a rubber or vinyl treaded ground-engaging surface for better traction and stability. However, these sandals, while doing an excellent job to immobilize the foot itself, are also extremely difficult for use in ambulation because of the unflexing, essentially flat configuration of the ground-engaging surface thereof, even occasionally irritating leg and hip joints and tendons.

During ambulation, of course the axis of the lower leg normally moves through an acute arch having an instantaneous fulcrum generally at the point of ground engagement beneath the ball of the sole of the foot. Likewise, during normal ambulation, the foot itself is allowed to flex in order to facilitate a smooth walking action. However, when the foot is immobilized from flexure by rigid platform postsurgical sandals, the ambulation process is substantially inhibited.

Because these conventional postsurgical sandals are relatively inexpensive to manufacture, and because they are intended for disposal after one-time use, such footwear remains as the most popular choice of the medical community for this purpose. However, a number of prior art inventions have recognized the need to facilitate somewhat of a more normal rocking action of the foot about some point of engagement to the ground. One such device having a broad ground-engaging surface is disclosed in U.S. Pat. No. 3,545,104 to Laurie for a walking cast protecting boot having a centrally located ground-engaging surface therewith. Another such device for use in conjunction with plaster casts is disclosed in U.S. Pat. No. 3,307,536 to Blosser; however, this invention includes structure adapted to be encapsulated and held against the sole and the foot and within the bottom of the walking cast. Yet another device for use in conjunction with foot casts is disclosed in U.S. Pat. No. 3,584,402 to Silverman, this sandal adapted to interengage around the plaster cast and to provide an elongated platform of diminishing thickness over the entire length of the rigid platform from heel to toe toward its toe support portion, thus also facilitating somewhat of a rocking motion of the ball of the foot during ambulation.

Still another device for use in conjunction only with walking casts is disclosed in U.S. Pat. No. 3,916,538 to Loseff disclosing a walking heel having a toe cover and having transverse grooves adapted to receive lengths of plaster of paris-impregnated material to assist in affixing the heel to the cast. This invention incorporates a curved ground-engaging surface over its entire length and substantially along the entire length of the sole of the foot to assist the patient in a heel-roll-over-toe gate.

U.S. Pat. Nos. 4,567,678 and 4,414,759 to Morgan et al. disclose a postoperative shoe having a unique ground-engaging surface also intended to permit the shoe to roll, imitating the natural motion of the foot during walking.

However, all of the inventions above described collectively fail to address the medical practitioners' needs in the first instance to avoid all flexure of both foot and its relationship to the lower leg immediately following surgery or treatment while later, after heeling has begun, satisfying the needs of the patient in more comfortable ambulation. To accomplish this dual-fold ambulation requirement based upon prior art, two separate pairs of post operative footwear would be required, both of which would be disposed of after one time use. Further, all of the devices discussed provide no means for adjusting or repositioning the ground-engaging fulcrum or pivotal point of the desired rocking motion of the foot to satisfy individual patients' needs.

The present invention provides a means for quickly and easily adapting a conventional postsurgical rigid platform sandal into one which facilitates normal foot and ankle rocking during ambulation at a point in time during recovery when the patient is determined to be able to handle such flexure and rocking motion after surgery.

BRIEF SUMMARY OF THE INVENTION

This invention is directed to a walking adapter connectable onto the ground-engaging surface or sole of a postsurgical sandal. The adapter comprises a rigid, configured support having a generally flat upper surface with adhesive means thereon for attachment transversely onto to the central portion of the sandal sole and a contoured lower surface which downwardly extends to its mid-portion. The mid-portion, relatively narrow and extending along the length of the adapter, is generally parallel to and spaced furthest from the upper surface and having ground-engaging surface texture. Various cross-section configurations and rib patterns are provided and the invention may also be releasably attachable for proper fore and aft adjustment and made lockably rotatable to modify the pivotal axis of the sandal during walking.

It is an object of this invention to provide a walking adapter for selective and individualized use in conjunction with conventional rigid platform postsurgical sandals.

It is another object of this invention to provide an inexpensive means for converting conventional rigid flat soled postsurgical sandals into more satisfactory rocking ambulatory footwear at a point and time following foot surgery when the medical practitioner determines that increased mobility will not inhibit recovery.

It is yet another object of this invention to retain the economic cost advantage of conventional postsurgical sandals while also facilitating an individualized incremental program to maximize ambulatory comfort during post foot surgery recovery.

In accordance with these and other objects which will become apparent hereinafter, the instant invention will now be described with reference to the accompanying drawings in which:

BRIEF DESCRIPTION OF THE DRAWINGS

FIG. 1 is a side elevation view of the invention attached to a conventional postsurgical sandal shown in phantom.

FIG. 2 is a bottom plan view of FIG. 1.

FIG. 3 is a perspective view of the preferred embodiment of the invention as shown in FIG. 1.

FIG. 4 is a section view in the direction of arrows 4—4 in FIG. 1.

FIG. 5 is a bottom plan view of another embodiment of the invention wherein the conventional sandal is shown in phantom.

FIG. 6 is a side elevation schematic view of yet another embodiment of the invention.

FIG. 7 is a side elevation schematic view of yet another embodiment of the invention.

FIG. 8 is a bottom plan view of yet another embodiment of the invention.

FIG. 9 is a section view in the direction of arrows 9—9 in FIG. 8.

DETAILED DESCRIPTION OF THE INVENTION

Referring now to the drawings, and particularly to FIGS. 1 through 4, the preferred embodiment of the invention is shown generally at 10 and includes a rigid configured support or block 12 preferably fabricated of contoured wood having a generally flat upper surface and a generally cylindrically contoured lower surface which, in the preferred embodiment, is semi-circular in cross section. The preferred embodiment 10 also includes an upper layer 18 of resilient rubber adhered to the upper surface of support 12 and a layer of adhesive 20 atop this upper layer 18.

The preferred embodiment 10 also includes a lower layer 14 adhered to the lower contoured surface of support 12 and also formed of resilient rubber. This lower layer 14 also includes a plurality of spaced apart ground-engaging ribs 16, a group 24 of which are always in ground-engaging contact during use.

The entire adapter 10, facilitated by adhesive layer 20, may be securely attached to the bottom surface B of the rigid generally flat platform P of a conventional postsurgical sandal S. These conventional sandals S include foot engaging material to secure them in place as shown in phantom.

As best seen in FIG. 1, the medical practitioner, when desiring to install the invention 10 in place at the appropriate time in the recovery cycle, may choose the appropriate fore and aft orientation of the adapter 10 for adhering into place as shown.

Also provided in the preferred embodiment 10 as best shown in FIG. 3 is a layer of nonadhering protective paper 22 which is kept in place until the invention 10 is ready for installation to protect adhesive 20.

By providing ribs 16 in spaced apart parallel relationship, a group 24 of these ribs 16, parallel to and furthest from the upper surface of support 12, securely contact the ground for enhanced traction without unduly limiting the rocking ambulatory benefits of this invention.

Referring now to FIG. 5, an alternate embodiment of the invention is shown generally at 30 having a structure similar to that previously described except that the lower resilient layer 32 includes diagonally disposed ribs 34 to provide a smoother ground-engaging contact as the adapter 30 and sandal S are pivotally rocked during ambulation.

Referring now to FIG. 6, yet another embodiment of the invention is shown schematically generally at 40, this embodiment structured similarly to that previously described except that the support 42 is fabricated of molded plastic rather than wood. This embodiment 40 features a narrower ground-engaging mid-portion 44 formed in cross section having a uniform radius R1 describing this mid-portion 44 longitudinally along the entire length of adapter 40. The remainder of the lower surface of adaptor 40 is defined by curvilinear segments 46 and 48.

Referring now to FIG. 7, another embodiment of the invention similar to that described in FIG. 6 is shown generally at 40 wherein a nonsymmetric ground-engaging mid-portion 54 of support 52 is shown having a smaller radius R2 defining one-half of the mid-portion 54 blending with larger radius R3 to form the other half of mid-portion 54. In this embodiment 50, generally in the form of a wedge, straight segments 56 and 58 form the remainder of the lower surface of support 52. By this embodiment 50, a variable rocking motion is achieved.

Referring lastly to FIGS. 8 and 9, another embodiment of the invention is shown generally at 60 which is intended to provide an angular adjustment for the ground-engaging mid-portion 78 such that it may be oriented either directly transversely with platform P or at an angle A thereto. To facilitate this angular adjusting and locking feature, a rigid mounting block 64 is provided which is releasably interengageable to platform P by hook and loop members 72 and 74. This releasable interengagement feature may be applied to the other embodiments of the invention for more easy fore and aft adjustment of the invention in relation to the platform P. Alternately, any of these embodiments may be connected to the bottom surface B of platform P by one or more nails or screws driven into the upper surface of the invention through platform P.

Mounting block 64 is pivotally connected by connector 66 to rigid support 62 and is made rotatably adjustable and lockable by the ball detent formed by protrusion 68 which is interengageable into one of a plurality of apertures 70. Although not shown, a ball and spring, in their well-known combination, may serve to form this resiliently movable protrusion 68. Lower layer 76, having longitudinal ribs as previously described and providing mid-portion 78 furthest from platform P, is fabricated generally as previously described with regard to FIG. 1.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A walking adapter for attachment to postsurgical sandals having a ground-engaging surface, comprising:

a rigid support having an upper generally flat surface, a lower arcuate surface and generally flat sides;

said upper surface sized to fit a central portion of the postsurgical sandal and having an adhesive thereon for securing said walking adapter in unlimited position as desired to the central portion of the ground-engaging surface of the postsurgical sandal;

said lower arcuate surface having a textured central portion extending across said walking adapter between said sides.

2. A walking adapter for postsurgical sandals as set forth in claim 1, wherein:

said ground-engaging surface texture includes a plurality of spaced parallel ribs.

3. A walking adapter for postsurgical sandals as set forth in claim 2, wherein;

said ribs are transverse.

4. A walking adapter for postsurgical sandals as set forth in claim 3, wherein:

at least three said ribs at a time engage the ground.

5. A walking adapter for postsurgical sandals as set forth in claim 1, wherein:

said ribs are diagonal.

6. A walking adapter for postsurgical sandals as set forth in claim 1, further comprising:

a lower layer of resilient material adhered to and covering at least said mid-portion;

said ground-engaging surface texture disposed on said lower layer.

7. A walking adapter for postsurgical sandals as set forth in claim 6, further comprising:

an upper layer of resilient material adhered to and covering said upper surface;

said adhesive means disposed on said upper layer.

8. A walking adapter for postsurgical sandals as set forth in claim 1, wherein:

said mid-portion has a constant cross section along substantially its entire length.

9. A walking adapter for postsurgical sandals as set forth in claim 8, wherein:

said constant cross section is formed having a smaller radious extending in one direction and a larger radius extending in the opposite direction from the region of said mid-portion furthest from said upper surface.

10. A walking adapter for postsurgical sandals as set forth in claim 8, wherein:

said constant cross section is formed having a constant radius.

11. A walking adapter for postsurgical sandals as set forth in claim 1, wherein:

said entire lower surface has a constant radius cross section along substantially its entire length.

12. A walking adapter for postsurgical sandals as set forth in claim 1, wherein:

said support is generally wedge-shaped in cross section along substantially its entire length.

13. A walk adapter for postsurgical sandals as set forth in claim 1, wherein:

said adhesive means is releasable and includes mating hook and loop members, one portion thereof connected to said upper surface, the other portion thereof connectable to the sandal ground engaging surface.

14. A walking adapter for postsurgical sandals comprising:

a rigid mounting block and a rigid, configured support, each having upper and lower surfaces;

said mounting block and said support pivotally connected such that said block lower surface and said support upper surface are mating against and pivotal one to another;

said mounting block upper surface having an adhesive means thereon for securely connecting said adapter to the bottom ground-engaging surface of the sandal;

said support lower surface contoured and having a mid-portion along substantially the entire length of said adapter and spaced generally furthest from and parallel to said support upper surface;

said mid-portion having ground-engaging surface texture and being disposed generally transverse to the sandal when said adapter is connected to the sandal;

a locking detent disposed between said mounting block lower surface and said support upper surface for pivotal adjustment of said mid-portion in relation to said mounting block and the sandal.

* * * * *